United States Patent
Hao et al.

(10) Patent No.: US 9,834,567 B1
(45) Date of Patent: Dec. 5, 2017

(54) CRYSTALLINE FORM OF CEFAMANDOLE NAFATE COMPOUND, PREPARATION AND PREPARING METHOD THEREOF

(71) Applicants: TIANJIN UNIVERSITY, Tianjin (CN); HAINAN LINGKANG PHARMACEUTICAL CO., LTD, Haikou (CN)

(72) Inventors: Hongxun Hao, Tianjin (CN); Linggang Tao, Haikou (CN); Fang He, Tianjin (CN); Baohong Hou, Tianjin (CN); Jingkang Wang, Tianjin (CN); Jun Lv, Hainan (CN); Qiuxiang Yin, Tianjin (CN); Yongli Wang, Tianjin (CN); Junbo Gong, Tianjin (CN); Chuang Xie, Tianjin (CN); Ying Bao, Tianjin (CN)

(73) Assignees: TIANJIN UNIVERSITY, Tianjin (CN); HAINAN LINGKANG PHARMACEUTICAL CO., LTD, Haikou (CN)

(*) Notice: Subject to any disclaimer, the term of this patent is extended or adjusted under 35 U.S.C. 154(b) by 0 days.

(21) Appl. No.: 15/687,359

(22) Filed: Aug. 25, 2017

Related U.S. Application Data

(63) Continuation-in-part of application No. 15/305,661, filed as application No. PCT/CN2015/095229 on Nov. 20, 2015.

(30) Foreign Application Priority Data

Dec. 16, 2014 (CN) .......................... 2014 1 0784492

(51) Int. Cl.
*C07D 501/36* (2006.01)
*C07D 501/12* (2006.01)

(52) U.S. Cl.
CPC ......... *C07D 501/36* (2013.01); *C07D 501/12* (2013.01); *C07B 2200/13* (2013.01)

(58) Field of Classification Search
CPC ........................... C07D 501/36; C07D 501/12
See application file for complete search history.

(56) References Cited

U.S. PATENT DOCUMENTS

| | | | | |
|---|---|---|---|---|
| 3,928,592 A | * | 12/1975 | Greene | A61K 9/0019 514/204 |
| 4,035,361 A | * | 7/1977 | Wheeler | C07D 501/36 540/220 |
| 2009/0227544 A1 | * | 9/2009 | Karpeisky | A61K 31/675 514/102 |

* cited by examiner

*Primary Examiner* — Kahsay Habte
(74) *Attorney, Agent, or Firm* — CBM Patent Consulting, LLC

(57) ABSTRACT

A novel crystalline form is defined by diffraction angle 2θ° of X-ray powder diffraction pattern and characteristic peak of differential scanning calorimetry (DSC). The novel crystalline form of Cefamandole Nafate is prepared as follows: adding Cefamandole Nafate in solid state to an organic solvent to form a suspension with a concentration of 0.04~0.3 g/ml, stirring the suspension at 40~50° C. for a period of time, and then cooling to 5~15° C. at certain cooling rate, continuing to stir for a period of time, then suction filtrating the obtained suspension, the resulting filer cake is Cefamandole Nafate as wet product, which is dried to constant weight to provide the novel crystalline form of Cefamandole Nafate as final product.

7 Claims, 2 Drawing Sheets

CRYSTALLINE FORM OF CEFAMANDOLE NAFATE COMPOUND, PREPARATION AND PREPARING METHOD THEREOF

This application is the continuation-in-part application claims priority to U.S. patent application Ser. No. 15/305,661 filed 21 Oct. 2016 that is the U.S. national phase of International Application No. PCT/CN2015/095229 filed on 20 Nov. 2015 which designated the U.S. and claims priority to Chinese Application Nos. CN201410784492.8 filed on 16 Dec. 2014, the entire contents of each of which are hereby incorporated by reference.

FIELD OF THE INVENTION

The invention belongs to the field of medicine separation technology, and in particular, relates to a novel crystalline form of Cefamandole Nafate compound and its preparing method.

PRIOR ART

Cefamandole Nafate has a chemical name of (6R, 7R)-7-R-(2-formyloxy-2-phenylacetamide)-3-[[(1-methyl-1H-tetrazol-5-yl) thio] methyl]-8-oxo-5-thia-1-azabicyclo[4.2.0] oct-2-ene-2-carboxylate sodium salt with a formula of $C_{19}H_{17}N_6NaO_6S_2$ and a molecular weight of 512.49, and the structure formula is shown in formula (I):

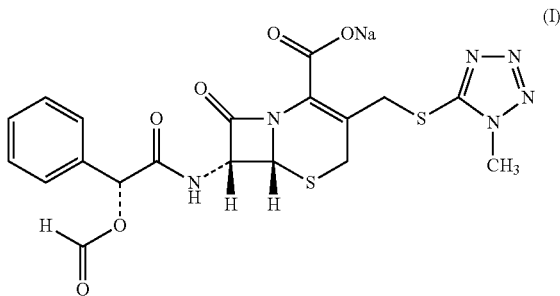

Cefamandole Nafate is researched and developed by Lilly Company of United American in 1972, and is sold firstly on market in 1978 with an injection tradename of MANDOL. Cefamandole Nafate is a second-generation semi-synthetic cephalosporin with strong bactericidal effect, and has certain advantages of the first-generation and the third-generation cephalosporins. Cefamandole Nafate is stable on β-lactamase, and has low nephrotoxicity, high blood concentration, good tissue penetration, and wide antibacterial spectrum. The main characteristics of Cefamandole Nafate lie in strong effect on Gram-negative bacteria, and relatively strong effects on anaerobic *clostridium*, meningococcal, *neisseria gonorrhoeae, escherichia coli, klebsiella pneumoniae, haemophilus* influenza, indole-positive *proteus* and so on, with most effective to *haemophilus*. Cefamandole Nafate is used for pulmonary infections caused by susceptible strains, urinary tract infections, biliary tract infections, skin and soft tissue infections, bone and joint infections, sepsis, abdominal infections and so on in clinical practice. As a safe and effective antimicrobial agent, Cefamandole Nafate is well tolerated, and has less adverse reactions.

In recent years, in order to improve the stability and bioavailability of Cefamandole Nafate, extensive research have been conducted by researchers on its polymorphs and pharmaceutical compositions, and currently published patent literatures include CN201210284600.6, CN201010257886.X, CN201010199235.X, CN201310021764.4 and so on. In Chinese patent CN201010257886.X and Chinese patent CN201010199235.X, hydrates of Cefamandole Nafate are prepared, while substances containing crystal water often appear defects of unstable crystal water during the formulation process, for example, Chinese patent CN201010257886.X discloses significantly decreased stability in long-term test and acceleration test, and Chinese patent CN201010199235.X discloses that sodium benzoate is added into claimed formulations, whereas sodium benzoate as a preservative has been banned in some countries for its security risk. Chinese patent 201210284600.6 discloses a product of Cefamandole Nafate, where the problem of solubility does not been solved because of many insoluble particles. Meanwhile, a lot of sodium carbonate, lidocaine, reduced glutathione or sodium glutamate are added in the formulation, and lidocaine and reduced glutathione are active drugs with uncertain security risks when they are used with Cefamandole Nafate.

DETAILED DESCRIPTION OF THE INVENTION

In order to solve the problems, the present invention discloses a novel crystalline form of Cefamandole Nafate having a melting range of 150~180° C. with the peak at 165±2° C. (the melting range of a common crystalline is between 90~100 V), thus the product has improved thermal stability and is non-perishable during the storage. Meanwhile, the crystalline form has an appearance of rough rod while a traditional stable crystalline form is tiny needle, so that the novel crystalline form has better fluidity and higher bulk density, which significantly improve the convenience of packaging and transportation.

The present invention discloses a novel crystalline form of Cefamandole Nafate, which has an X-ray powder diffraction pattern having characteristic peaks expressed in degrees 2θ at 4.0±0.2, 4.7±0.2, 6.2±0.2, 7.5±0.2, 9.9±0.2, 10.8±0.2, 14.5±0.2, 15.8±0.2, 16.3±0.2, 17.4±0.2, 18.1±0.2, 19.2±0.2, 20.1±0.2, 21.4±0.2, 22.2±0.2, 22.8±0.2, 23.9±0.2, 24.9±0.2, 30.1±0.2, and 34.1±0.2, as shown in FIG. 1.

Said crystalline form of Cefamandole Nafate has a differential scanning calorimetry thermogram (DSC) having an endothermic peak at 165±2° C., as shown in FIG. 2.

Said crystalline form of Cefamandole Nafate has a crystal appearance as shown in FIG. 3.

A method for preparing the crystalline form of Cefamandole Nafate crystal is as follows: adding Cefamandole Nafate in solid state to an organic solvent to form a suspension with a concentration of 0.04~0.3 g/ml, stirring the suspension at 40~50° C. for a period of time, then cooling to 5~15° C. at certain cooling rate, continuing to stir for a period of time, and suction filtrating the obtained suspension, the resulting filer cake is Cefamandole Nafate as wet product, which is dried to constant weight to provide the novel crystalline form of Cefamandole Nafate as final product.

Said organic solvent is selected from one of methanol, ethanol, n-propanol, isopropanol, n-butanol, isobutanol, sec-butanol, iso-pentanol, n-pentanol, ethyl acetate, 1, 4-dioxane and acetone or a mixture thereof.

In said method, the stirring rate of the suspension is 600~1200 r/min.

In said method, the stirring time of the suspension before cooling is 5~10 h.

In said method, the stirring time of the suspension after cooling is 5~10 h.

In said method, the cooling rate of the suspension is 0.2~2° C./min.

In said method, the drying is carried out for 6~12 h under normal pressure at a temperature of 20~70° C.

Said method has the following advantageous effects: simple procedure, easy operation, and low energy consumption. The prepared product has a melting range of 160~170° C. with good thermal stability, and is conducive to the long-term preservation. The product has a purity of 99% or above with a yield of 90% or higher, and the purity, the color and the appearance do not make any change after 100 days storing at normal temperature under dry condition. The product is easy to crush and processed into dosage forms of a pharmaceutical composition, as well as low cost, and easier to implement on commercial and industrial scale.

The novel crystalline form of Cefamandole Nafate obtained from said method has higher melting point and better thermal stability than those of reported forms, without degradation after placing for a long time. The product has better form, higher bulk density, better mobility, more uniform particle size distribution, and more conducive to post-treatment, which make great advantages in pharmaceutical formulations. Meanwhile, the product has a high purity and a high process yield.

It is shown on toxic reactions that the novel crystalline form of Cefamandole Nafate compound provided in the present invention has decreased toxicity than that of existing Cefamandole Nafate.

EMBODIMENTS OF THE INVENTION

The present invention is further illustrated by the following figures and examples. By these illustration, features and advantages of the present invention becomes clearer and more definite.

Example 1

Figure 1:
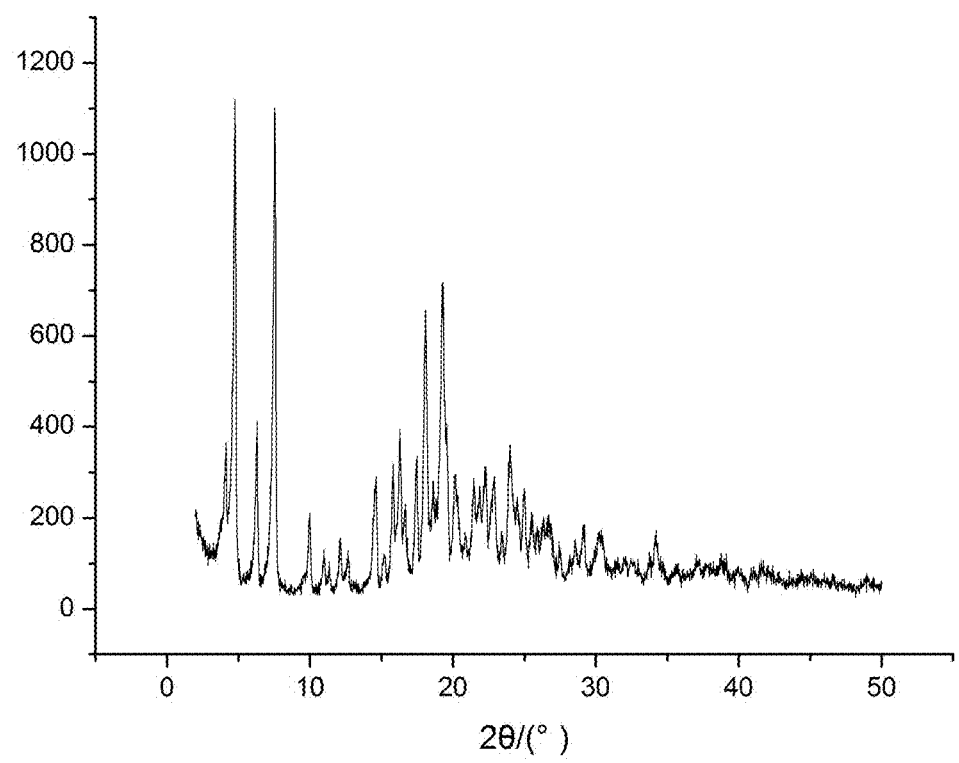
FIG. 1 shows the X-ray powder diffraction pattern of the novel crystalline form of Cefamandole Nafate compound.
Figure 2:
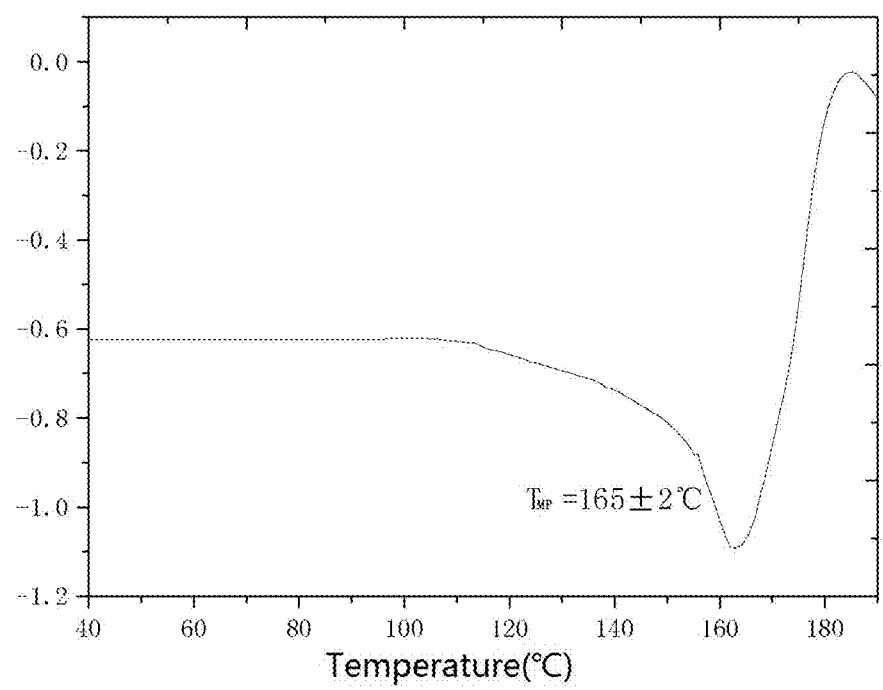
FIG. 2 shows the differential scanning calorimetry thermogram of the novel crystalline form of Cefamandole Nafate compound.
Figure 3:
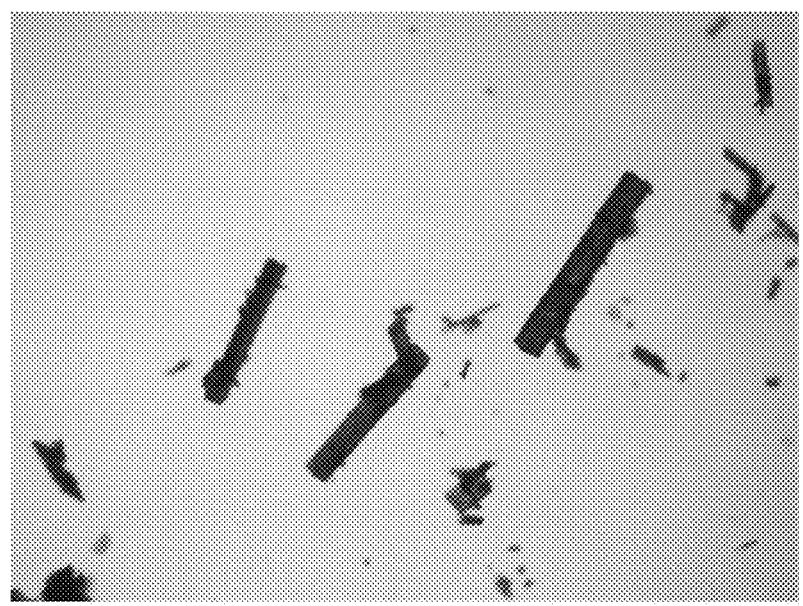
FIG. 3 shows the microphotograph of the novel crystalline form of Cefamandole Nafate compound.

0.40 g of Cefamandole Nafate as dried solid was added to 10 mL of 1, 4-dioxane to form a suspension, stirring the suspension at 600 r/min and heating to 40° C., continuing to stir for 5 h under constant temperature, and then cooling the suspension down to 5° C. at a cooling rate of 0.2° C./min and stirring for 5 h under constant temperature, vacuum filtrating the crystal slurry, and the residue was dried at 20° C. and under normal pressure for 6 h to constant weight, to obtain a product of novel crystalline form of Cefamandole Nafate. The XRD pattern of the product was shown in FIG. 1, having characteristic peaks expressed in degrees 2θ at 4.01, 4.66, 6.18, 7.47, 9.95, 10.70, 14.56, 15.82, 16.26, 17.40, 18.05, 19.26, 20.15, 21.45, 22.25, 22.78, 24.00, 24.94, 30.17, and 34.16. The DSC thermogram was shown in FIG. 2, having an endothermic peak at 164° C. The product of the novel crystalline form provided by this method had a melting point, which is about 69° C. higher than that of a common crystal form, with higher thermal stability, and without degradation after placing for a long time. The product had an appearance of rough rod shown in FIG. 3, with a purity of 99.2% and a process yield of 92.8%.

Example 2

0.43 g of Cefamandole Nafate as dried solid was added to 4 mL of methanol to form a suspension, stirring the suspension at 800 r/min and heating to 45° C., continuing to stir for 8 h under constant temperature, and then cooling the suspension down to 10° C. at a cooling rate of 1° C./min and stirring for 9 h under constant temperature, vacuum filtrating the crystal slurry, and the residue was dried at 40° C. and under normal pressure for 10 h to constant weight, to obtain a product of novel crystalline form of Cefamandole Nafate. The XRD pattern of the product had characteristic peaks expressed in degrees 2θ at 4.04, 4.70, 6.22, 7.48, 9.90, 10.80, 14.66, 15.72, 16.22, 17.38, 18.02, 19.20, 20.08, 21.38, 22.12, 22.82, 23.88, 24.92, 30.32, 34.16. The DSC thermogram had an endothermic peak at 166° C. The product of the novel crystalline form provided by this method had a melting point, which is about 71° C. higher than that of a common crystal form, with higher thermal stability, and without degradation after placing for a long time. The product had an appearance of rough rod, with a purity of 99.1% and a process yield of 92%.

Example 3

0.50 g of Cefamandole Nafate as dried solid was added to 10 mL of ethyl acetate to form a suspension, stirring the suspension at 1000 r/min and heating to 48° C., continuing to stir for 9 h under constant temperature, and then cooling the suspension down to 15° C. at a cooling rate of 1° C./min and stirring for 8 h under constant temperature, vacuum filtrating the crystal slurry, and the residue was dried at 60° C. and under normal pressure for 10 h to constant weight, to obtain a product of novel crystalline form of Cefamandole Nafate. The XRD pattern of the product had characteristic peaks expressed in degrees 2θ at 4.10, 4.76, 6.28, 7.54, 9.98, 10.61, 14.46, 15.62, 16.30, 17.46, 18.08, 19.28, 20.16, 21.48, 22.26, 22.84, 24.00, 24.98, 30.26, 34.22. The DSC thermogram had an endothermic peak at 164° C. The product of the novel crystalline form provided by this method had a melting point, which is about 69° C. higher than that of a common crystal form, with higher thermal stability, and without degradation after placing for a long time. The product had an appearance of rough rod, with a purity of 99.6% and a process yield of 92.8%.

Example 4

0.60 g of Cefamandole Nafate as dried solid was added to 4 mL of acetone to form a suspension, stirring the suspension at 1000 r/min and heating to 50° C., continuing to stir for 8 h under constant temperature, and then cooling the suspension down to 12° C. at a cooling rate of 0.5° C./min and stirring for 10 h under constant temperature, vacuum filtrating the crystal slurry, and the residue was dried at 50° C. and under normal pressure for 8 h to constant weight, to obtain a product of novel crystalline form of Cefamandole Nafate. The XRD pattern of the product had characteristic peaks expressed in degrees 2θ at 4.02, 4.68, 6.20, 7.46, 9.90, 10.90, 14.66, 15.92, 16.50, 17.36, 18.00, 19.20, 20.08, 21.40, 22.18, 22.78, 23.90, 24.88, 30.16, 34.14. The DSC thermogram had an endothermic peak at 167° C. The product of the novel crystalline form provided by this method had a melting point, which is about 72° C. higher than that of a common crystal form, with higher thermal stability, and without degradation after placing for a long time. The product had an appearance of rough rod, with a purity of 99.4% and a process yield of 93.5%.

Example 5

5.00 g of Cefamandole Nafate as dried solid was added to 25 mL of a mixed solution of 1, 4-dioxane and ethanol (2:3, in volume) to form a suspension, stirring the suspension at 1200 r/min and heating to 50° C., continuing to stir for 7 h under constant temperature, and then cooling the suspension down to 10° C. at a cooling rate of 1.5° C./min and stirring for 9 h under constant temperature, vacuum filtrating the crystal slurry, and the residue was dried at 45° C. and under normal pressure for 7 h to constant weight, to obtain a product of novel crystalline form of Cefamandole Nafate. The XRD pattern of the product had characteristic peaks expressed in degrees 2θ at 4.08, 4.74, 6.26, 7.52, 9.94, 10.60, 14.35, 15.60, 16.26, 17.42, 18.08, 19.26, 20.12, 21.40, 22.26, 22.90, 23.96, 24.96, 30.30, 34.20. The DSC thermogram had an endothermic peak at 165° C. The product of the novel crystalline form provided by this method had a melting point, which is about 70° C. higher than that of a common crystal form, with higher thermal stability, and without degradation after placing for a long time. The product had an appearance of rough rod, with a purity of 99.1% and a process yield of 92.5%.

Example 6

3.00 g of Cefamandole Nafate as dried solid was added to 10 mL of a mixed solution of 1, 4-dioxane and acetone (1:1, in volume) to form a suspension, stirring the suspension at 1200 r/min and heating to 50° C., continuing to stir for 10 h under constant temperature, and then cooling the suspension down to 15° C. at a cooling rate of 2° C./min and stirring for 10 h under constant temperature, vacuum filtrating the crystal slurry, and the residue was dried at 70° C. and under normal pressure for 12 h to constant weight, to obtain a product of novel crystalline form of Cefamandole Nafate. The XRD pattern of the product had characteristic peaks expressed in degrees 2θ at 4.10, 4.74, 6.26, 7.52, 9.96, 10.65, 14.65, 15.72, 16.28, 17.42, 18.08, 19.28, 20.16, 21.50, 22.18, 22.90, 24.00, 24.98, 30.32, 34.26. The DSC thermogram had an endothermic peak at 163° C. The product of the novel crystalline form provided by this method had a melting point, which is about 68° C. higher than that of a common crystal form, with higher thermal stability, and without degradation after placing for a long time. The product had an appearance of rough rod, with a purity of 99.3% and a process yield of 94.2%.

Toxic Reaction Tests

The novel crystalline form of Cefamandole Nafate compound of the present invention was tested by toxic reaction tests shown as follows (taking the crystalline form of Cefamandole Nafate obtained in Example 1 for example):

Mice were divided into 4 dose groups by weights, every 10 animals in each group, and administered by intravenous injection, subcutaneous injection and intraperitoneal injection with a concentration of 3350, 3380, 3850, 4400, 4500, 5200, 5700, and 7000 mg/mL. The $LD_{50}$ in mice through intravenous, subcutaneous, intraperitoneal injection was 4216 mg/kg, 7256 mg/kg and 4500 mg/kg, respectively, and the $LD_{50}$ in rats was 3425 mg/kg through intravenous injection.

Rabbits were injected with 0.4~2.1 g of Cefamandole Nafate each time with the interval of 15 min, and recording the changes of blood pressure and electrocardiogram. After anesthesia, Cefamandole Nafate was administrated to rabbits through intravenous injection, and the blood pressure dropped 0~37 mmHg with breathing deepened and accelerated, while the electrocardiogram and heart rate did not change significantly. When the dosage up to 4800 mg/kg, the blood pressure significantly decreased, and the respiration was inhibited, with the electrocardiogram prolonged in P-R interval, depressed in ST segment, and ventricular arrhythmias. Further increased the dosage, death occurred in rabbits.

Rabbits were divided into 2 groups, every 4 animals in each group, and daily intravenously injected with 250 mg/kg Cefamandole Nafate for 15 days, while the control group was injected with 5 ml saline per day. The results showed that the renal tissue concentration of Cefamandole Nafate increased in rabbits, although the renal toxicity is low.

Referring to the novel crystalline form of Cefamandole Nafate compound and its preparation method which are disclosed and provided in the present invention, with using the present invention for reference, a person skilled in the art could make it implemented by altering materials and process parameter properly. Method and product of the present invention has already been illustrated by preferable embodiments, it will be apparent for related technicians to make changes, modifications and combinations according to the method and product provided by the present invention to achieve technology realization in the present invention, without deviating from the content, spirit and scope of the present disclosure. Especially, all of the similar replacements and modifications are obvious for those skilled in the art, which will be seen to fall within the spirit, scope and content of the present invention.

What is claimed is:

1. A method for preparing a crystalline form of Cefamandole Nafate having an X-ray powder diffraction pattern having characteristic peaks expressed in degrees 2θ at 4.0±0.2, 4.7±0.2, 6.2±0.2, 7.5±0.2, 9.9±0.2, 10.8±0.2, 14.5±0.2, 15.8±0.2, 16.3±0.2, 17.4±0.2, 18.1±0.2, 19.2±0.2, 20.1±0.2, 21.4±0.2, 22.2±0.2, 22.8±0.2, 23.9±0.2, 24.9±0.2, 30.1±0.2, and 34.1±0.2 and a differential scanning calorimetry thermogram (DSC) having an endothermic peak at 165±2° C., characterized in that: adding Cefamandole Nafate in solid state to an organic solvent to form a suspension with a concentration of 0.04~0.3 g/ml, stirring the suspension at 40~50° C., then cooling to 5~15° C. and stirring, and suction filtrating the obtained suspension, the resulting filer cake is Cefamandole Nafate as wet product, which is dried to constant weight to provide the crystalline form of Cefamandole Nafate.

2. The method according to claim 1, characterized in that, said organic solvent is selected from one of methanol, ethanol, n-propanol, isopropanol, n-butanol, isobutanol, sec-butanol, iso-pentanol, n-pentanol, ethyl acetate, 1, 4-dioxane and acetone or a mixture thereof.

3. The method according to claim 1, characterized in that, the stirring rate of the suspension is 600~1200 r/min.

4. The method according to claim 1, characterized in that, the stirring time of the suspension before cooling is 5~10 h.

5. The method according to claim 1, characterized in that, the stirring time of the suspension after cooling is 5~10 h.

6. The method according to claim 1, characterized in that, the cooling rate of the suspension is 0.2~2° C./min.

7. The method according to claim 1, characterized in that, the drying is carried out for 6~12 h under normal pressure at a temperature of 20~70° C.

\* \* \* \* \*